(12) United States Patent
Orr et al.

(10) Patent No.: US 8,696,591 B2
(45) Date of Patent: Apr. 15, 2014

(54) COMPENSATION OF VOLUMETRIC ERRORS IN A GAS MONITORING SYSTEM

(71) Applicants: Joseph A. Orr, Park City, UT (US); Craig T. Flanagan, New York, NY (US)

(72) Inventors: Joseph A. Orr, Park City, UT (US); Craig T. Flanagan, New York, NY (US)

(73) Assignee: RIC Investments, LLC, Wilmington, DE (US)

( * ) Notice: Subject to any disclaimer, the term of this patent is extended or adjusted under 35 U.S.C. 154(b) by 0 days.

(21) Appl. No.: 13/652,581

(22) Filed: Oct. 16, 2012

(65) Prior Publication Data

US 2013/0041280 A1 Feb. 14, 2013

Related U.S. Application Data

(62) Division of application No. 11/948,080, filed on Nov. 30, 2007, now Pat. No. 8,312,878.

(51) Int. Cl.
*A61B 5/08* (2006.01)

(52) U.S. Cl.
USPC .......................................... 600/532; 600/531

(58) Field of Classification Search
USPC .................................. 600/529–543
See application file for complete search history.

(56) References Cited

U.S. PATENT DOCUMENTS

| 4,221,224 | A * | 9/1980 | Clark ............................ 600/531 |
| 5,789,660 | A | 8/1998 | Kofoed |
| 6,312,389 | B1 | 11/2001 | Kofoed |
| 6,325,978 | B1 | 12/2001 | Labuda |
| 6,616,896 | B2 | 9/2003 | Labuda |
| 6,632,402 | B2 | 10/2003 | Blazewicz |
| 6,815,211 | B1 | 11/2004 | Blazewicz |
| 6,888,101 | B2 | 5/2005 | Davis |
| 6,954,702 | B2 | 10/2005 | Pierry |
| 7,301,125 | B2 | 11/2007 | Davis |
| 7,335,164 | B2 | 2/2008 | Mace |
| 2002/0029003 | A1 * | 3/2002 | Mace et al. ................ 600/532 |
| 2002/0095096 | A1 | 7/2002 | Mault |
| 2006/0009707 | A1 | 1/2006 | Daniels |
| 2006/0145078 | A1 | 7/2006 | Russell |

OTHER PUBLICATIONS

Welch et al. "Measurement of metabolic rate in hyperoxia". J Appl Physiol 51:725-731, 1981.*

* cited by examiner

*Primary Examiner* — Patricia Mallari
*Assistant Examiner* — Christian Jang (57) ABSTRACT

A mainstream gas monitoring method includes a using a mainstream airway adapter and a gas sensing assembly associated with the mainstream airway adapter to measure an analyte of a gas flow through the adapter. A gas sensing portion outputs a signal indicative of the analyte in a gas flow in the mainstream airway adapter. A processing portion receives the signal from the gas sensing portion and determines an amount of the analyte in the gas flow based on the signal from the gas sensing portion. The processing portion also compensates for volumetric differences between the gas flow during inspiration and the gas flow during expiration to maximize the accuracy in the measurements.

8 Claims, 8 Drawing Sheets

COMPENSATION OF VOLUMETRIC ERRORS IN A GAS MONITORING SYSTEM

Under the provisions of 35 U.S.C. §120/365, this application is a Divisional of U.S. patent application Ser. No. 11/948,080, filed Nov. 30, 2007.

TECHNICAL FIELD

The present invention pertains to a system and method for compensating for volumetric changes that may occur in a mainstream gas monitoring system between inspiration and expiration to (a) maximize the accuracy of an oxygen consumption measurement and (b) provide a more clinically relevant waveform for the monitored gas when using a mainstream gas monitoring system.

BACKGROUND OF THE INVENTION

Airway oxygen monitoring, or oxygraphy, is used in anesthesia and critical care situations to provide an indication of oxygen delivery to and utilization (i.e. oxygen consumption) by the patient. The difference between inspired and end-tidal oxygen fraction is useful to determine, for example, the amount of oxygen extraction which serves as a measure of cardiac and pulmonary function (e.g. adequacy of perfusion and metabolism) and overall physiologic condition of the patient. Oxygen consumption is commonly used to monitor the fitness or physiological condition of an individual or athlete. The phrases "oxygen update" and "oxygen consumption" are used synonymously, and are both represented by the expression "$V_{O_2}$," or, for simplicity "$VO_2$". Oxygen consumption is a measure of the amount of oxygen that the body uses in a given period of time, such as one minute. It is typically expressed as milliliters of oxygen used per kilogram of body weight per minute (ml/kg/min), simply in milliliters of oxygen used per minute.

Traditionally, oxygraphy is accomplished using a sidestream gas sampling system. In a sidestream monitoring system, a gas sample is taken from a sample site, such as the patient's airway via a nasal cannula or a patient circuit through a gas sampling line, to a sensing mechanism or sample cell that is located some distance from the sample site for monitoring. A drying system is typically included in the cannula, sample cell, or sampling line so that sidestream flow of gas entering the sample cell is relatively moisture free. If the drying system consists of a section of Nafion tubing, the gas sample is dried to ambient humidity. Similarly, the transport of the gas through the sampling line results in the temperature of the sample equilibrating to the ambient temperature prior to analysis by the sensor. For these reasons, both inspired and expired gas, are analyzed in side-stream monitoring systems as if the gas was at ambient temperature and humidity.

When oxygraphy is performed using an on-airway oxygen sensor (i.e., a mainstream gas sensor in which all or most the gas delivered to or received from the patient passes through the sample site), the gas being analyzed will likely vary in both temperature and humidity. The expired gas is nearly always 100% saturated (relative humidity=100%) and at body temperature or slightly below body temperature. On the other hand, the inspired gas may be actively heated and humidified using a vaporizer, may be passively humidified using a heat-moisture exchanger, or may be at ambient conditions. In any case, it is unlikely that the intra-airway temperature and humidity data will be available to the oxygen monitor.

As gas is humidified and water vapor is added to the gas, the oxygen in the gas is diluted and the concentration of oxygen in the gas decreases. If inspired gas is dry and expired gas is humidified, the oxygraph measured by an on-airway (mainstream) oxygen sensor will show a difference in inspired and expired oxygen just based on the changes of oxygen concentration due to warming and/or humidification. While the oxygen concentration measurement is physically accurate, it is clinically misleading. Even though there is an actual difference in inspired and expired oxygen fraction, this difference could be misinterpreted as an indication of patient perfusion and metabolism, rather than simple gas warming and humidification.

$VO_2$ is conventionally calculated as the difference between the volume of oxygen inspired and the volume of oxygen expired. The standard or direct calculation of $VO_2$ is given by the following equation:

$$VO_2 = Vi * Fi_{O2} - Ve * \overline{Fe}_{O2}, \qquad (1)$$

where: "$VO_2$" is oxygen consumption, "Vi" is inspired volume, "$Fi_{O2}$" is the inspired oxygen concentration, "Ve" is the expired volume, and "$\overline{Fe}_{O2}$" is the mixed expired oxygen concentration. An error occurs in this calculation if the expired gas has been heated and moistened by the lungs, and the inspired gas is cooler and/or drier than the expired gas. The effect of heating and/or humidification means that the expired volume (Ve) will be larger than the inspired volume (Vi) and the measured expired oxygen fraction ($\overline{Fe}_{O2}$) will be lower than the actual oxygen fraction, leading to a falsely large $VO_2$ determination. Ideally, if it were possible to measure the inspired oxygen fraction ($Fi_{O2}$) and inspired volume (Vi) under known temperature and humidity conditions, then the direct $VO_2$ calculation would be accurate despite the differences in temperature and humidity between inspired and expired gasses.

This direct calculation of oxygen consumption described in equation (1) is simple and valid, but it can lead to errors in the calculated $VO_2$ in situations where there are small errors in the gas volume measurement, i.e., the measurement of Vi, Ve, or both. Gas temperature and humidity differences are a major source of these inspired-expired gas volume differences. This problem is exacerbated at high oxygen concentrations.

An alternative method of calculating $VO_2$ uses only the expired breath volume, Ve. In this scenario, the inspired breath volume Vi is calculated (rather than measured) based on the assumption that, on average, the nitrogen volume is the same for both inspired and expired gas, which is usually true because nitrogen is not consumed or produced by the body. This is referred to as the nitrogen balance. The calculation of Vi, rather than measuring it, also assumes that the effect of temperature and humidity are the same for both inspired and expired gas volumes.

This modification of equation (1), which uses a calculation of Vi based on the nitrogen balance noted above, is known as the Haldane transform. According to this technique, Vi is calculated as follows:

$$Vi = Ve * \overline{Fe}_{N2} / Fi_{N2} \qquad (2)$$

Where "$\overline{Fe}_{N2}$" is the concentration of mixed expired nitrogen, and "$Fi_{N2}$" is the concentration of mixed inspired nitrogen. The nitrogen concentration can be calculated as the balance gas (or gas that is neither oxygen or $CO_2$, both of which are directly measured) assuming that the only gases in the airways are oxygen, carbon dioxide, and nitrogen. Based on this, the Haldane transform becomes:

$$Vi = Ve * (1 - \overline{Fe}_{CO2} - \overline{Fe}_{O2}) / (1 - Fi_{CO2} - Fi_{O2}), \qquad (3)$$

and the oxygen consumption calculation becomes:

$$VO_2 = Ve^*[Fi_{O2}^*((1-\overline{Fe}_{CO2}-\overline{Fe}_{O2})/(1-Fi_{CO2}-Fi_{O2}))-\overline{Fe}_{O2}], \quad (4)$$

where $\overline{Fe}_{CO2}$ is the mixed expired carbon dioxide concentration, and $Fi_{CO2}$ is the mixed inspired carbon dioxide concentration.

Calculating $VO_2$ using the Haldane transform has the advantage that the effects of errors in volume measurements that are not "common mode" are eliminated, because only the expired volume measurement is used. Common mode errors are errors that affect both the Vi and Ve measurements, such as a calibration error in a flow sensor. Assuming, of course, the same sensor is used to measure Ve and Vi.

As noted above, expired volume is often larger than inspired volume because the exhaled gas is warmed and humidified by the lungs. When the Haldane transform is used, the added volume due to temperature and humidity causes an invalid estimation of Vi when the $Fi_{O2}$ is measured in dry gas, which leads to an erroneously high calculated Vi and $VO_2$.

This is typically not a problem when a conventional side-stream gas sampling system is used to measure $Fi_{O2}$, $\overline{Fe}_{O2}$, $Fi_{CO2}$, and $\overline{Fe}_{CO2}$, because conventional side-stream gas sampling systems typically include a gas drying system, as noted above.

If, however, a mainstream monitoring system is used to measure $Fi_{O2}$, $\overline{Fe}_{O2}$, $Fi_{CO2}$, and $\overline{Fe}_{CO2}$, the use of the inspired-expired temperature and humidity differences can lead to an error. In a mainstream monitoring system, the sampling site is located in-situ in a patient circuit or conduit coupled to the patient's airway. As a result, the patient's expired gases are normally saturated with water vapor and have a temperature of about 35° C. If the inspired gas is cooler and/or drier than the expired gas, errors result in the $VO_2$ calculation using either the direct or Haldane transform equations. Using the direct calculation method, it would be necessary to correct both the inspired oxygen fraction ($Fi_{O2}$) and the inspired volume (Vi) to expired gas temperature and humidity conditions to make a correct calculation. Using the Haldane transform, only the inspired oxygen fraction must be corrected to the same warm and wet conditions as seen in expired gas for the calculation to be valid.

DISCLOSURE OF THE INVENTION

The present inventors recognized that oxygraphy data acquired from an on-airway sensor would be more useful clinically, if the signal could be modified such that inspired and expired data is displayed as if both were at the same conditions of temperature and humidity. To this end they developed a means for correcting the oxygraphy waveform such that inspired and expired portions of the waveform are displayed as if both were at the same conditions by compensating for volumetric measurements of oxygen without the use of intra-airway temperature and humidity measurements.

Accordingly, it is an object of the present invention to provide a gas monitoring system that overcomes the shortcomings of conventional gas monitoring system and that can be used as a mainstream gas monitor. This object is achieved according to one embodiment of the present invention by providing a mainstream gas monitoring system that includes a mainstream airway adapter, and a gas sensing assembly associated with the mainstream airway adapter. The gas sensing assembly includes a gas sensing portion associated with the mainstream airway adapter and a processing portion. The gas sensing portion is configured and arranged to output a signal indicative of an analyte in a gas flow in the mainstream airway adapter. The processing portion receives the signal from the gas sensing portion and determines an amount of the analyte in the gas flow based on the signal from the gas sensing portion. The processing portion also compensates for volumetric differences between the gas flow during inspiration and the gas flow during expiration.

It is yet another object of the present invention to provide a method of monitoring system an analyte in a gas flow using a mainstream gas monitoring system that does not suffer from the disadvantages associated with conventional analyte monitoring techniques. This object is achieved by providing a method that includes (1) providing mainstream airway adapter having a gas flow therethrough; (2) producing a signal indicative of an analyte in the gas flow; (3) determining an amount of the analyte in the gas flow based on the signal from the gas sensing portion; (4) compensating for volumetric differences between the gas flow during inspiration and the gas flow during expiration; and (5) providing a signal indicative of the amount of analyte in a human perceivable format.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
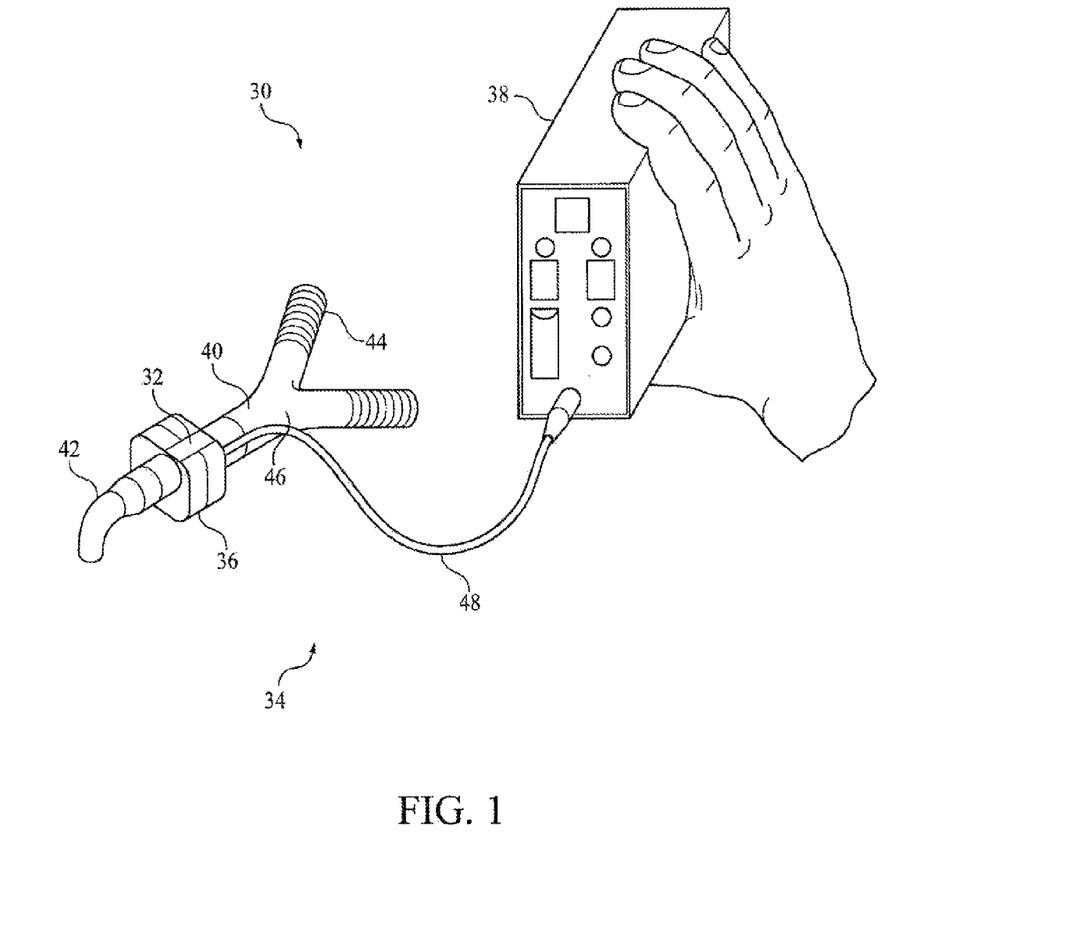
FIG. 1 is a perspective view of a first embodiment of a gas sensing system according to the principles of the present invention.

FIG. 1 schematically illustrates an exemplary embodiment of a mainstream gas monitoring system 30 according to the principles of the present invention. Gas monitoring system 30 includes an airway adapter 32 and a gas sensing assembly, generally indicated at 34. Airway adapter 32 is disposed in a respiratory circuit 40, which is used to communicate a flow of gas to a patient. For example, a first end 42 of respiratory circuit 40 includes a patient interface appliance configured to communicate with an airway of a patient. Examples of patient interface appliances that are suitable for use with respiratory circuit 40 include, but are not limited to: an endrotracheal tube, a nasal cannula, a tracheotomy tube, a mask, or any other device or apparatus that communicates a flow of gas with an airway of a user.

A second end 44 of respiratory circuit 40 is configured to communicate with a gas source. For instance, the gas source may include ambient atmosphere, a supply of pressurized gas, a pressure support device, a ventilator, or other sources of gas. In the illustrated embodiment, a Y-connector 46, which is typically found in a ventilator circuit, is shown connected to the second end of the airway adapter. One leg of the Y-connector corresponds to the inspiratory limb, which delivers gas from a ventilator (not shown) to the patient, and the other leg of the Y-connector corresponds to the expiratory limb, which delivers gas from the patient. Typically, the gas is delivered by the expiratory limb back to the ventilator, which is the gas source in this embodiment. In a single limb system, a single conduit communicates a flow of gas between the patient and the gas source, which is often a pressure support system, such as a CPAP, bi-level, or auto-titrating pressure support device.

Figure 2:
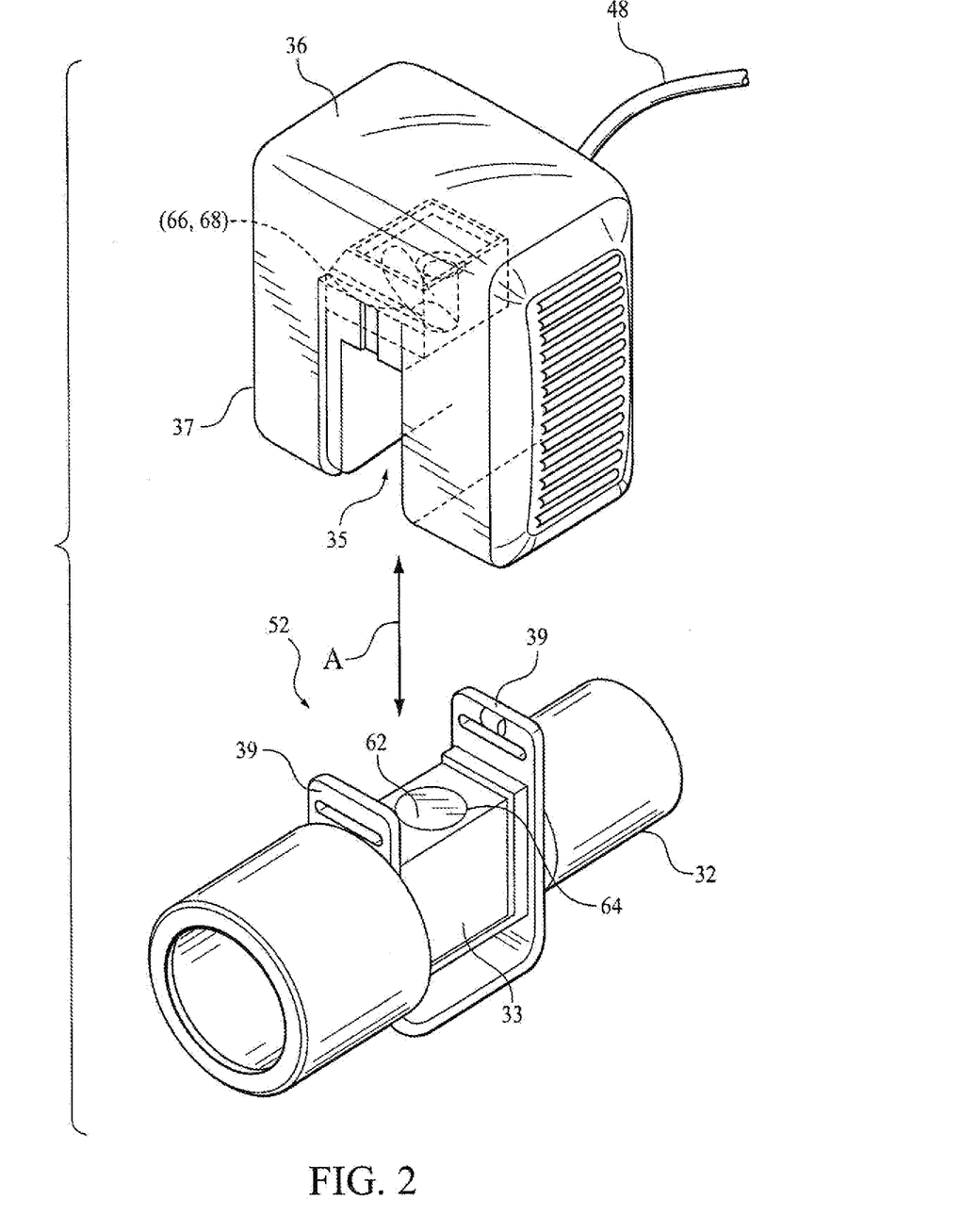
FIG. 2 is a perspective view of an airway adapter and gas sensor in the gas sensing system of FIG. 1.
Figure 3:
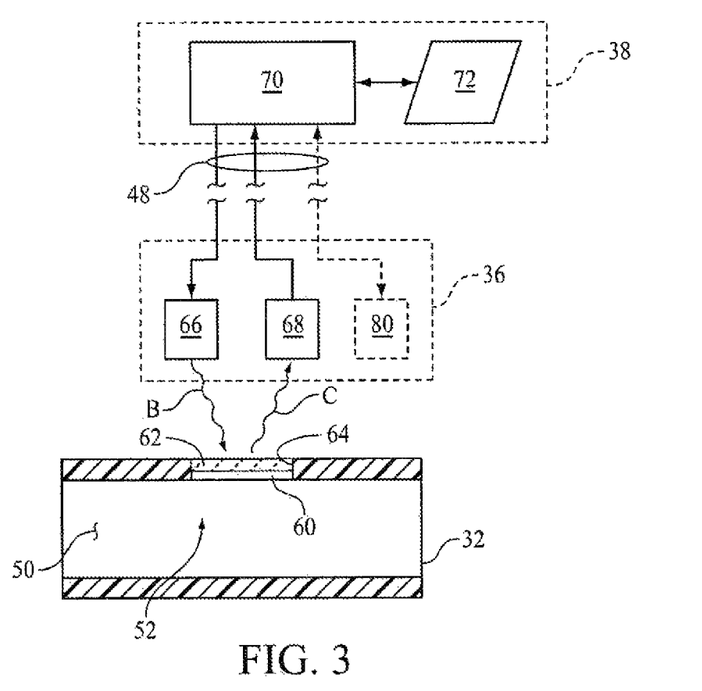
FIG. 3 is a schematic view of the components of the gas sensing system of FIG. 1.

As perhaps best shown in FIGS. 2 and 3, airway adapter 32 provides a flow path 50 in-line with respiratory circuit 40 through which gas passes to and from the patient. The airway adapter also provides a gas monitoring portion or sample site, generally indicated at 52, at which the constituents of the gas passing through the airway adapter are monitored or measured. Examples of airway adapter suitable for use in the present invention are described in U.S. Pat. Nos. 5,789,660 ("the '660 patent"); 6,312,389 ("the '389 patent"), and 7,335,164 ("the '164 patent"), the contents of each of which are incorporated herein by reference.

In the embodiment illustrated in FIGS. 1-3, gas sensing assembly 34 includes a gas sensing portion 36 and a processing portion 38. In this illustrated exemplary embodiment, gas sensing portion 36 is removably coupled to airway adapter 32, as indicated by arrow A, and includes the components that are used to detect the gas constituent or constituents, also referred to as analyte, being monitored. It should be appreciated that a variety of mechanisms may be implemented to removably couple gas sensing portion 36 to airway adapter 32. In an exemplary embodiment shown in FIG. 2, a seating area 33 is provided on an outer surface of airway adapter 32 that is adapted to securely receive a housing 37 of gas sensor portion 36. Housing 37 is generally "U" shaped to fit onto seating area 33 with a channel 35 that receives the generally matching shape of the seating area of the airway adapter. Flanges 39 can be provided on the airway adapter to align and attach the housing to the airway adapter. U.S. Pat. Nos. 6,616,896 ("the '896 patent") and 6,632,402 ("the '402 patent"), the contents of each of which are incorporated hereby by reference, describe techniques for coupling gas sensing portion 36 to airway adapter 32. The present invention also contemplates permanently connecting gas sensing portion 36 to airway adapter 32 so that the functionality of each component is effectively combined into a common element.

A communication link 48 allows data, power, and any other signals, commands, etc. to be communicated between gas sensing portion 36 and processing portion 38. Although a hard wired communication link 48 is shown in FIGS. 1-3, it is to be understood that the present invention contemplates that the communication link can be a wireless link, using any form of wireless communication or communication protocol. Of course, if a wireless link is provided, a power supply, such as battery, must be included in gas sensing portion 36 or a power must be provided in some other manner to the gas sensing portion.

Gas sensing assembly 34 detects the concentration of one or more gases (analytes) in the flow of gas through the sample cell. In an exemplary embodiment illustrated in FIGS. 1-3, gas sensing assembly 34 is configured to employ luminescence quenching techniques to measure the partial pressure or amount of oxygen or other gases that flow through airway adapter 32. This oxygen measurement is used (in conjunction with flow), for example, to determine the values for inspired and mixed expired fractions of oxygen ($Fi_{O2}$ and $\overline{Fe}_{O2}$).

Luminescence quenching is a technique that has been used to measure oxygen concentrations in gases. In using luminescence quenching to measure oxygen concentrations, a luminescable material 60 is excited to luminescence by delivering an excitation energy, as indicated by arrow B, to the luminescable material. Upon being excited to luminescence, the luminescable material will emit energy, as indicated by arrow C. However, when the luminescing material is exposed to a gas mixture including oxygen, the luminescence is quenched and the luminescable material will emit less energy, as indicated by arrow C, depending upon the amount (i.e., concentration or fraction) of oxygen to which the luminescable material is exposed, or the amount of oxygen in the gas mixture. Accordingly, the rate of decrease in the amount of luminescence, or quenching of luminescence, of the luminescable material (i.e., the amount of light emitted by the luminescable material) corresponds to the amount of oxygen in the gas mixture. Thus, the energy emitted by the luminescable material can be used to determine the concentration of the gas passing through the airway adapter. U.S. Pat. Nos. 6,325,978; 6,632,402; 6,616,896; and 6,815,211, the contents of each of which are incorporated herein by reference, all disclose an example of an oxygen sensor that uses luminescence quenching to determine the concentration of a gas, such as oxygen, in the gas flowing through a sample cell.

As shown in FIGS. 1-3, a quantity of luminescable material 60 is situated such that it is exposed to the gas flowing in flow path 50 through airway adapter 32. The present invention also contemplates providing a combination of luminescable materials in communication with the gas flowing through the airway adapter. Porphyrins are an example of a material that may be used as luminescable material 60. Porphyrins are stable organic ring structures that often include a metal atom. When the metal atom is platinum or palladium, the phosphorescence decay time ranges from about 10 μs to about 1,000 μs. Porphyrins are also sensitive to molecular oxygen. When porphyrins are used as luminescable material 60, it is preferred that the porphyrins retain substantially all of their photo-excitability with repeated use. Stated another way, it is preferred that the porphyrins be "photostable". Fluorescent porphyrins, such as meso-tetraphenyl porphines, are particularly photostable. The various types of porphyrins that may be used as luminescable material 232 to facilitate oxygen detection include, without limitation, platinum meso-tetra(pentafluoro)phenyl porphine, platinum meso-tetraphenyl porphine, palladium meso-tetra(pentafluoro)phenyl porphine, and palladium meso-tetraphenyl porphine. Of course, other types of luminescable materials that are known to be quenched upon being exposed to oxygen, carbon dioxide, or another analyzed substance (e.g., gas, liquid, or vapor) may also be used in airway adapters incorporating teachings of the present invention.

In the illustrated embodiment, luminescable material 60 is provided on airway adapter 32, and a window 62 is provided in an opening 64 in the body of the airway adapter to allow excitation energy B to be transmitted to the luminescable material. Window 62 preferably has a high transmittance for wavelengths of excitation radiation, which excite luminescable material 60, as well as for wavelengths of radiation C emitted from luminescable material. For example, window 62 may be formed of sapphire, one or more polymers (e.g., polyethylene, etc.), a glass, and/or other substantially transparent materials.

In an exemplary embodiment, luminescable material 60 is carried by a membrane or matrix, which is disposed on or comprises an integral part of a surface or wall of the airway adapter defining gas flow path 50. The present invention also contemplates that the luminescable material and associated components, such as a membrane, need not be directly coupled to the airway adapter, but can be selectively coupled so that the luminescable material can be replaced without having to remove or replace the entire airway adapter.

An emitter 66 is provided in gas sensing portion 36 to emit excitation energy B to luminescable material 60. In an exemplary embodiment of the present invention, the energy emitted by emitter 66 includes electromagnetic radiation with a wavelength that causes luminescable medium 60 to luminance. Emitter 66 may include one or more Organic Light Emitting Diodes ("OLEDs"), lasers (e.g., diode lasers or other laser sources), Light Emitting Diodes ("LEDs"), Hot Cathode Fluorescent Lamps ("HCFLs"), Cold Cathode Fluorescent Lamps ("CCFLs"), incandescent lamps, halogen bulbs, received ambient light, and/or other electromagnetic radiation sources.

In one exemplary implementation, emitter 66 includes one or more green and/or blue LEDs. These LEDs typically have high intensity in the luminescable composition absorption region of luminescable medium 60 and output smaller amounts of radiation at other wavelengths (e.g., red and/or infrared). This minimizes stray interfering light and photodegradation of the sensor. While, the present invention is by no means limited to the use of LEDs, other advantages of implementing LEDs as emitter 30 include their light weight, compactness, low power consumption, low voltage requirements, low heat production, reliability, ruggedness, relatively low cost, and stability. Also they can be switched on and off very quickly, reliably, and reproducibly.

A detector 68 is provided in gas sensing portion 36 to detect radiation C. Detector 68 is positioned within gas sensing portion 36 such that when gas sensing portion 3 and airway adapter 32 are coupled, detector 68 receives at least a portion of luminesced electromagnetic radiation C from luminescable medium 60. Based on the received radiation, detector 60 generates one or more output signals related to one or more properties of the received radiation. For example, the one or more output signals may be related to an amount of the radiation, an intensity of the radiation, a modulation of the radiation, and/or other properties of the radiation. In one embodiment, detector 68 includes a PIN diode. In other embodiments, other photosensitive devices are employed as detector 68. For instance, detector 68 may take the form of a diode array, a CCD chip, a CMOS chip, a photo-multiplier tube and/or other photosensitive devices.

Luminescable medium 60, in response to radiation B from emitter 66, emits electromagnetic radiation C in a substantially omni-directional manner at a wavelength different from that of the electromagnetic radiation provided by the emitter. The intensity and/or persistence of this luminesced electromagnetic radiation rises and falls according to the relative amounts of one or more analytes, such as oxygen, included in the body of gas within gas flow path 50. In one embodiment, oxygen causes a modification of the intensity and/or persistence of luminescent radiation B by quenching the luminescence reaction. As the concentration of oxygen increases, the modification of the intensity and/or persistence of luminescent radiation B decreases. In one embodiment, luminescable medium 60 is formed as a luminescent film. For example, both of the incorporated '896 and '402 patents disclose films that may be employed as luminescable medium 60.

Based on the output signal from gas sensing portion 36, processing portion 38 determines information related to one or more properties of one or more analytes or constituents included in the gas disposed within flow path 50. In the illustrated exemplary embodiment, processing portion 38 includes a processor 70 that controls emitter 66 and receives the signal from detector 68. Processor 70 uses the signal from detector 68 to determine the oxygen concentration as discussed in detail below. Although not shown, processor 70 and/or processing portion 38 may include other components typically used to monitor gas constituents, such as memory (RAM, ROM).

As shown in FIG. 3, the present invention contemplates that processing portion 38 includes an input/output device 72 or devices for providing an output of processor 70 in a human perceivable format. In an exemplary embodiment, input/output device 72 is a monitor or display that visually indicates the oxygen concentration to the user. The present invention also contemplates that input/output device 72 includes communication elements, such as terminals, transceivers, modems, etc. for communicating an output of processor 70 to a remote location. This can be done wirelessly, via a hardwire communication system, or using any combination thereof.

Figure 4:
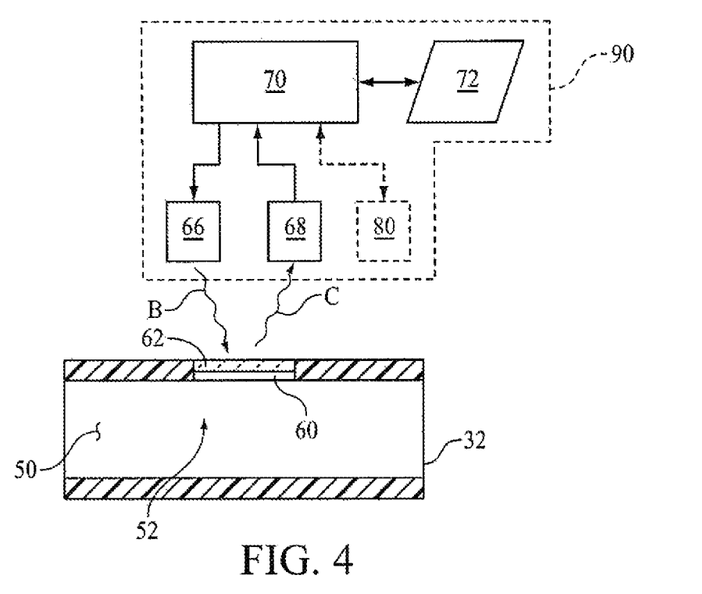
FIG. 4 is schematic view of the components of a second embodiment of a gas sensing system according to the principles of the present invention.
Figure 5:
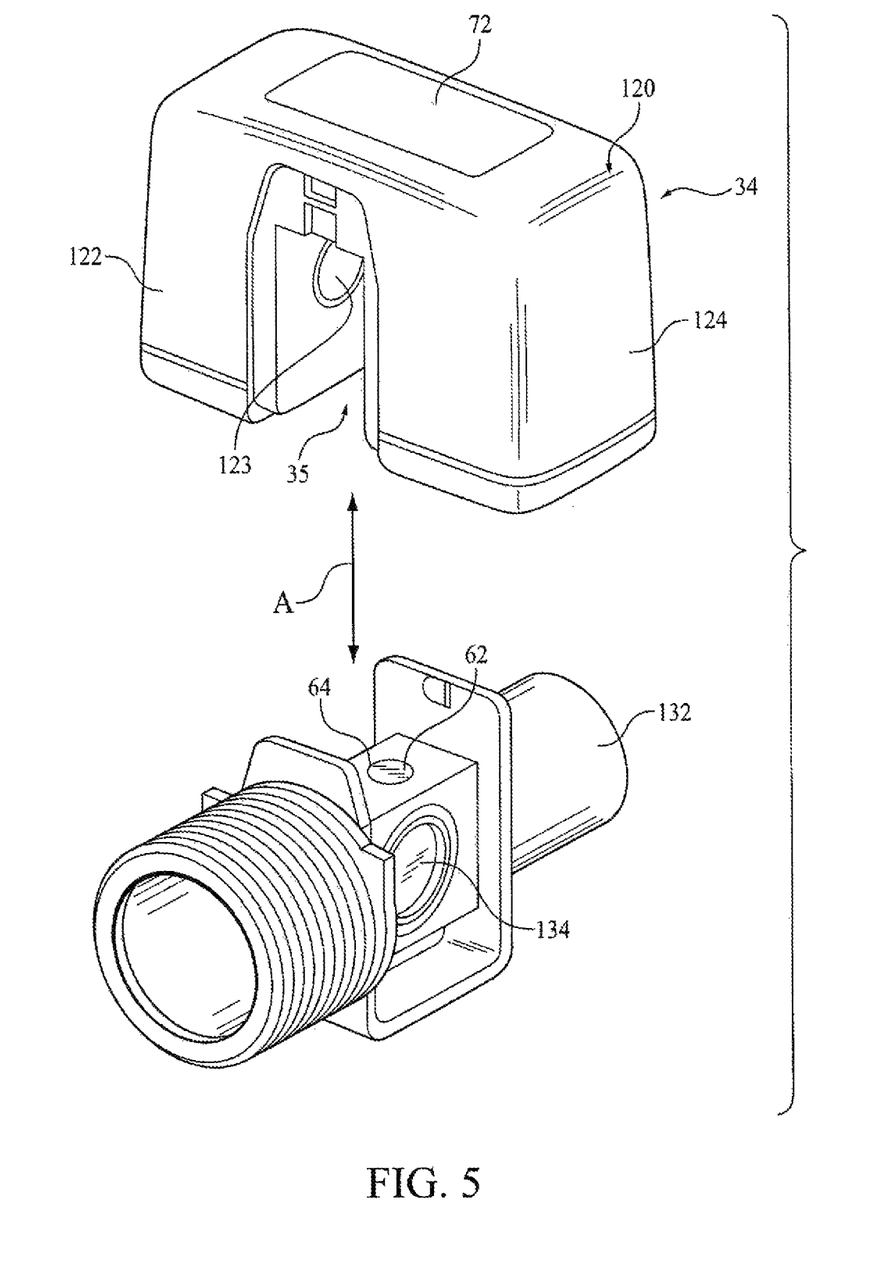
FIG. 5 is a perspective view of an airway adapter and gas sensor according to a third embodiment of the present invention.

In the embodiments of FIGS. 1-3, gas sensing portion 36 and processing portion 38 are separate structures that contain their respective components. The present invention also contemplates that these two portions can be combined into a common gas sensing/processing portion 90, as shown schematically in FIG. 4 and in FIG. 5. That is, all of the components necessary to detect, monitor, determine, display, and communicate information pertaining to the gas concentration, such as $VO_2$ can be provided in the sensor head 90 that attaches to airway adapter 32. An example of a sensor head 95 having such functionality is shown in FIG. 5 and is disclosed, for example, in U.S. patent application Ser. No. 11/368,832 (publication no. US-2006-014078-A1), the contents of which are incorporated herein by reference.

The present invention contemplates that additional components can be used in gas sensing portion 36. For example, one or more filter elements can be positioned within the gas sensing portions, e.g., between luminescable medium 60 and detector 68. Such filter elements 42 are typically designed to prevent electromagnetic radiation that is not emitted by the luminescable medium from becoming incident on the detector. For instance, in one embodiment, the filter elements are wavelength specific and permit luminescence radiation C to pass therethrough to become incident on detector 68 while substantially blocking radiation with other wavelengths.

Other components that can be used in gas sensing portion 36 include a reference detector and a beam splitting element that directs a portion of the radiation propagating toward detector 68 onto the reference detector. One or more output signals generated by the reference detector may be provided to processor 70 and used as a reference to account, and compensate, for system noise (e.g., intensity fluctuations in emitter 66, etc.) in the signals generated by detector 68.

In some implementations, gas sensing portion 36 may include one or more optical elements (not shown) to guide, focus, and/or otherwise process radiation emitted by emitter 66 or provided to detector 68. For example, one or more lenses may collimate the radiation in a selected direction. As more particular examples, both of the incorporated '896 and '402 patents disclose the use of optical elements that process radiation emitted by an emitter similar to emitter 66.

The present invention further contemplates using a thermal capacitor to maintain luminescable medium 60 at a substantially constant operating temperature to reduce or eliminate inaccuracies in gas measurement system 30 attributable to variations in the temperature of the luminescable medium. Thus, the thermal capacitor is any device that accomplishes this function, such as a heater controlled in a feedback fashion based on an output of a temperature sensor, a heat sink, or the like. Examples of suitable thermal capacitors in the form of heating elements are disclosed in U.S. Pat. No. 6,888,101 and in U.S. Pat. No. 7,301,125, the contents of each of which are incorporated hereby by reference.

In the embodiment illustrated in FIGS. 1-4, a single window 62 is provided on the airway adapter. The present invention also contemplates providing two windows similar to window 62 in the airway adapter. As is shown and described in the '402 patent, the two windows may be disposed in airway adapter 32 opposite from each other to enable electromagnetic radiation to pass through the adapter. In this embodiment, a detector 32 may be positioned on an opposite side of the airway adapter from emitter 66 when sensor.

The present invention also contemplates that airway adapter 32 can include other one or more additional gas measuring and/or sensing components. These other sensing components are schematically illustrated as 80 in FIG. 3. Examples of such sensors includes temperature, light, sound, humidity, pressure, flow, and gas concentration sensors. Such sensors can be used to monitor the flow of gas, gas sensing portion 36 or both. For example, a temperature sensor can be provided in housing 37 to detect overheating in the housing. A temperature sensor can also be provided to detect the temperature of the gas flowing in the airway adapter.

FIG. 5 illustrates a gas monitoring system that includes both a carbon dioxide ($CO_2$) concentration detecting capability and an oxygen ($O_2$) concentration detecting capability. The oxygen concentration detecting system corresponds to the luminescence quenching technique discussed above and includes a luminescable material disposed on window 62 of an airway adapter 132. The $CO_2$ monitoring system is an absorption type gas (analyte) detection system in which energy is transmitted from an emitter (not shown) disposed on one leg of a housing 120 (such as leg 122). A window 123 is shown on an interior surface of leg 122 from which the energy exits housing 120. The energy is provided to a first window (not shown) defined in the airway adapter. It passes through a gas sample (the gas flowing through gas flow path 50), and out a second window 134 also defined in the airway adapter generally opposite the first window. The energy exiting the sample site via second window 134 is measured by a detector (not shown) provided in second leg 124.

As known in the art, the signal from the detector is used to determine the gas (analyte) concentration. For example, it is known to use the output of this type of absorption system to detect the amount of $CO_2$ in the gas passing through the airway adapter, which is used to determine the amount of mixed expired $CO_2$ ($\overline{Fe}_{CO2}$) and the amount of inspired $CO_2$ ($Fi_{CO2}$). The signal from the detector can be processed by a processor provided in housing 37 or sent wirelessly or via a hardwire 48 to a separate processing portion. In this illustrated embodiment, the processing portion is incorporated into housing 120 and the resultant analyte measurement is shown on display 72.

In a similar fashion, the present invention further contemplates that the airway adapter can be configured to include a flow sensing system to measure the flow or flow rate of gas passing through the airway adapter. The flow rate is used to determine the amount of analyte passing through the airway adapter over a given period of time or during a respiratory cycle or phase thereof.

One type of flow sensing system suitable for use in this embodiment of the present invention is a pneumotach type of flow sensor. Such a flow sensor includes a flow element (not shown) that is disposed in the gas flow path so as to create a pressure drop in the flow of gas along the gas flow path. The pressure drop created by the flow element is measured and used to determine the flow rate.

Figure 6:
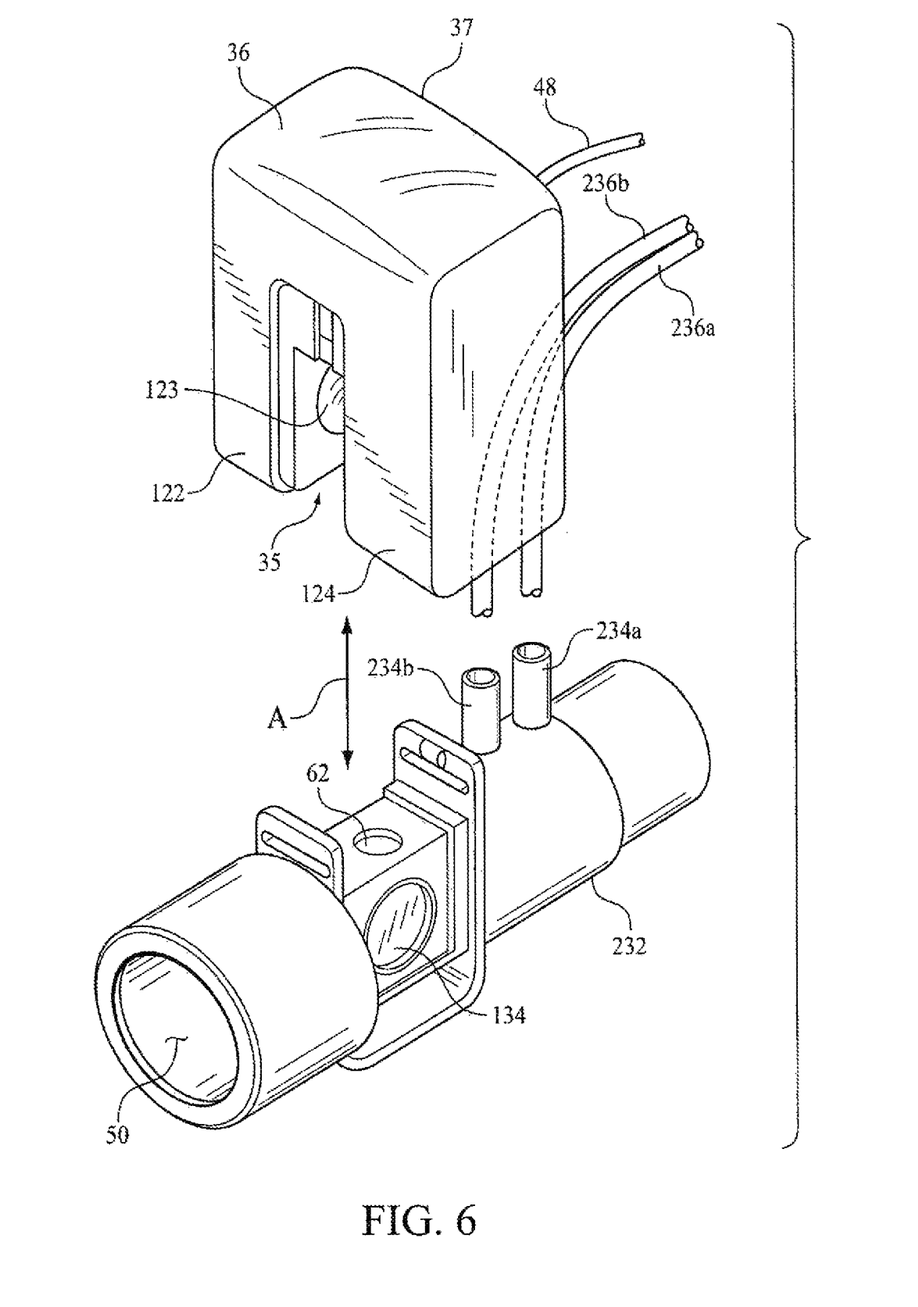
FIG. 6 is a perspective view of an airway adapter and gas sensor according to a still further embodiment of the present invention.

FIG. 6 illustrates an airway adapter 232 having such a flow sensing capability. It should be noted that airway adapter also has an $O_2$ and $CO_2$ sensing capability using the techniques discussed above. Airway adapter 232 includes a pair of ports 234a and 234b that are provided on each side of the flow element contained within the airway adapter. These pressure sensing elements allow the pressure drop across the flow element to be measured so that the flow of gas through the airway adapter can be measured quantitatively. For example, a pair of tubes or pneumatic hoses 236a and 236b can be coupled to ports 234a and 234b to and to a pressure sensor or sensors in processing portion 38 (see FIG. 1). The pressure sensors measure the pressure drop and this output is used to determine the flow through the airway adapter.

In the embodiment illustrated in FIG. 6, the additional flow sensing function is not contained in housing 37, which also contains at least some components of analyte sensing system. However, the present invention also contemplates that the flow sensing elements, such as the pressure sensor(s) and processor can be contained in housing 37. In which case, ports 234a and 234b would be coupled directly to the housing. In the embodiment illustrated in FIG. 6, the flow element is provided on one side of the gas measurement site. The present invention also contemplates using the gas measurement site to create the pressure drop. In which case, ports 234a and 234b would be provided on either side of the gas measurement cite. Such a configuration is taught, for example, in the '660 patent, the '389 patent, and the '451 application.

Because mainstream oxygen sensing systems measure the oxygen in the primary gas flow, i.e., the flow of gas in gas flow path 50, such systems do not include any significant gas drying or dehumidification components. As a result, the effect that temperature and humidity have on the inspired and expired gas, namely the increase in volume of the exhaled gas, must be taken into consideration in order to obtain an accurate oxygen consumption measurement using the Haldane transform.

To compensate for the lack of any significant gas drying or dehumidification components, the present invention determines how much gas volume has been added due to temperature and humidification increases present in the expired gas and takes this into consideration in calculating $VO_2$. In short, the present invention, corrects the error by correcting the inspired oxygen fraction measured using a mainstream sensor to the same temperature and humidity conditions as the expired gas.

The percent increase in volume due to increased temperature and humidify is estimated by analyzing the oxygen fraction expired from the tracheal dead space ($Fi_{O2\_DS}$) as compared to the inspired oxygen fraction ($Fi_{O2}$). The tracheal dead space gas is essentially inspired gas that has been warmed and humidified in the trachea, but has not participated in alveolar gas exchange. By using the oxygen concentration as measured in the tracheal dead space gas, instead of the oxygen concentration as measured in the inspired gas, the present invention effectively corrects both gases to the same conditions. The tracheal dead space oxygen concentration $Fi_{O2\_DS}$ is substituted into the Haldane transform and the $VO_2$ calculation as follows:

$$Vi=Ve*(1-\overline{Fe}_{CO2}-\overline{Fe}_{O2})/(1-Fi_{CO2}-Fi_{O2\_DS}), \text{and} \quad (5)$$

the oxygen consumption calculation becomes:

$$VO_2=V_E*[Fi_{O2\_DS}*(1-\overline{Fe}_{CO2}-\overline{Fe}_{O2})/(1-Fi_{CO2}-Fi_{O2\_DS}))-\overline{Fe}_{O2}]. \quad (6)$$

In the event that inspired oxygen concentration is not stable or constant during inspiration, the ratio of $Fi_{O2\_DS}$ to $Fi_{O2}$ can be applied to the $Fi_{O2}$ signal over the complete inspiration. Alternatively, the difference can between $Fi_{O2\_DS}$ and $Fi_{O2}$ can be added (or subtracted) from the $Fi_{O2}$ signal over the complete inspiration. Note that the $Fi_{O2}$ signal used in calculating the ratio, or difference, should correspond to the gas at the end of inspiration that remained in the tracheal dead space at the end of inspiration.

In the event that the inspired gas is heated and humidified to the same degree as expired gas, then the ratio of dead-space $F_{O2}$ to inspired $Fi_{O2}$ will be 1.0. If the inspired gas is completely dry and at room temperature, and the expired gas is fully humidified at 37° C., then the ratio will be 0.902.

To make the comparison correctly, the $Fi_{O2}$ that is analyzed should be the same gas that is analyzed from the tracheal dead space. This means that the $Fi_{O2}$ should be calculated using the last gas to enter the lungs and corresponding to the volume of the tracheal dead space as measured, for example, using Fowlers method.

Figure 7:
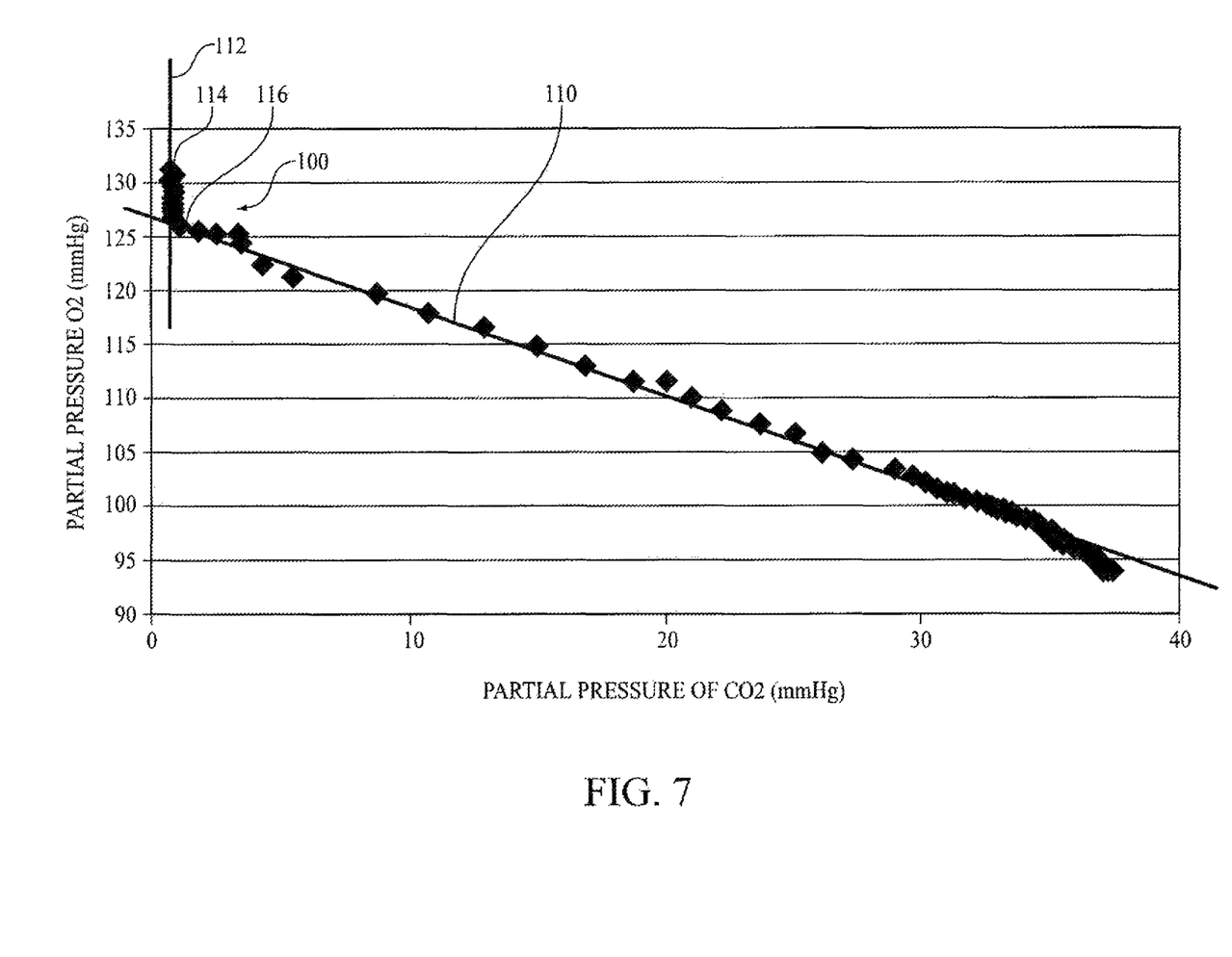
FIG. 7 is a chart showing the relationship between the partial pressure of CO2 and O2 during exhalation.

FIG. 7 is a graph that shows the $CO_2$ partial pressure plotted against the oxygen partial pressure during expiration only. At the beginning of expiration, generally indicated at 100, the oxygen partial pressure falls while the $CO_2$ partial pressure remains constant. This is the effect of heating and humidification of the tracheal gas. Thus, the oxygen partial pressure at 100 corresponds to $Fi_{O2\_DS}$. This plot corresponds to dry room temperature inhaled gas and exhaled gas at room temperature.

An exemplary method of detecting the $Fi_{O2\_DS}$ value is to draw the line using linear regression of the corresponding partial pressure value of the $CO_2$ vs. $O_2$ plot using only the data when $CO_2$ is greater than a threshold (i.e. 0.5% $CO_2$). See line 110 in FIG. 7. The point where line 110 intersects the average $O_2$ concentration of the gas that remained in the tracheal dead-space at the end of inspiration, line 112, is the oxygen fraction of the gas in the tracheal dead-space ($Fi_{O2\_DS}$). For the breath illustrated by the plot shown in FIG. 7, this intersection occurs at point 116, so that $Fi_{O2\_DS}$ is approximately 126 mm Hg.

It can also be appreciated from reviewing FIG. 7, that the $Fi_{O2}$ at the start of expiration, which is indicated at 114, is about 131 mm Hg. This corresponds to oxygen concentration peak of the CO2 v. O2 plot shown in FIG. 7. Shortly after the start of inspiration, the tracheal deadspace gas has been expelled and the gas that was exchanged in the lungs begins exits the patient. Thus, the partial pressure of oxygen drops. At the point where the $CO_2$ beings to increase, the exhaled gas is no longer tracheal deadspace gas. In the example shown in FIG. 7, the ratio of dead-space $F_{O2}$ to inspired $Fi_{O2}$ ($Fi_{O2\_DS}/Fi_{O2}$) is approximately 126/131=0.962. As noted above, if this ratio is "1", there is substantially no error due to gas heating/humidification.

Figure 8:
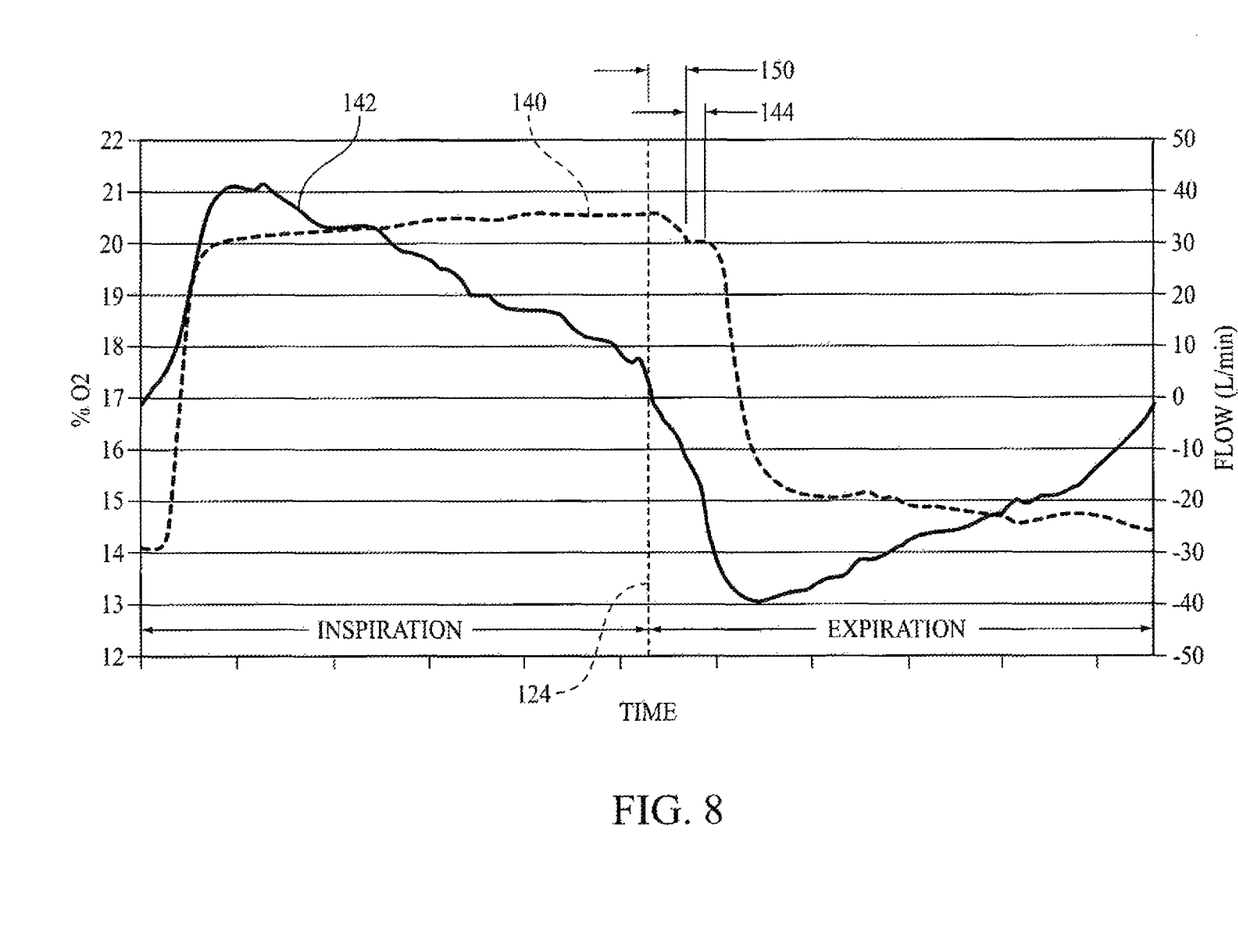
FIG. 8 is a graph showing an exemplary oxygen percent waveform and an exemplary flow waveform over a single breath illustrating how the oxygen concentration measurement changes due to gas heating and/or humidification.

FIG. 8 is a graph of an exemplary oxygen concentration waveform 140 and an exemplary gas flow waveform 142 over a single breath. This figure illustrates how the oxygen gas concentration, as measured by a mainstream gas monitoring system located near the patient, changes during a typical respiratory cycle. The transition from inspiration to expiration, which occurs when the flow rate crosses the "zero" point, is indicated by dashed line 144. During a time period 150 immediately at the start of expiration, the oxygen concentration falls slightly because the gas being expelled by the patient is gas from the oral cavity, which has not participated in the gas exchanged in the lungs and has only mixed slightly with the gas that has been exchanged in the lungs. This gas also has not been heated/humidified to any appreciable extent. During a time period 152, gas from the tracheal dead space gas, which has been heated/humidified is expelled from the patient. This heated/humidified gas, which the associated volumetric error causes a shift in the oxygen concentration measurement during this period. The oxygen concentration at this point is the $Fi_{O2\_DS}$ value.

In an exemplary embodiment of the present invention, the $O_2$ and $CO_2$ signals are measured as close to simultaneously as possible and are sampled at the generally same point or location in the breathing circuit. The present invention also contemplates that the flow signal be aligned in time with the $CO_2$ and $O_2$ signals. Selecting the gas that remained in the tracheal dead-space requires knowledge of the volume of the tracheal dead-space. This volume can be determined using Fowlers method. Fowlers method, originally described by Fowler for nitrogen (Fowler, W. S. (1948), "Lung function studies II: the respiratory dead-space", Am. J. Physiol., 154: 405-410)), has been applied to carbon dioxide by researchers, such as Fletcher et al. (Fletcher, R., Jonson, B., Cumming, G. & Brew, J. (1981), "The Concept of Deadspace With Special Reference to the Single Breath Test for Carbon Dioxide," Br. J. Anaesth., 53: 77-88). As an example, Fowlers method is implemented in the NICO2® monitoring device sold by RESPIRONICS, Inc. of Murrysville, Pa.

The present invention also contemplates using the techniques disclosed herein to trigger an alarm indicating that heating and or humidification of the inspired gas is not adequate. The standard of clinical care in the ICU is to heat and humidify the inspired gas. If gas is properly heated and humidified, then there will be little or no difference between $Fi_{O2\_DS}$ and $Fi_{O2}$. The presence of a significant difference between $Fi_{O2\_DS}$ and $Fi_{O2}$ may be used to trigger an alarm or message indicating a problem with the heating and humidification of the inspired gas.

This same principle could be applied using any gas so long as the gas is present in significant quantity in the inspired gas and can be analyzed and aligned with the flow signal. For example, analysis of the concentration difference between inspired and tracheal dead-space nitrogen, nitrous oxide, helium etc., could be used to detect a difference in heat and humidification between inspired and expired gas. $CO_2$ could be used if it were present in the inspired gas, such as in $CO_2$ a rebreathing maneuver.

In another embodiment, the correction can be applied to direct calculation of $VO_2$ (equation (1)) by substituting $Fi_{O2\_DS}$ for $Fi_{O2}$. Even though this correction may not be optimal, it would correct much of the error associated with gas temperature and humidity differences. Making this substitution in equation (1) yields the following:

$$VO_2=Vi*Fi_{O2\_DS}-Ve*\overline{Fe}_{O2} \quad (7)$$

The present invention also contemplates using the techniques disclosed herein to correct the oxygram waveform. The compensation of the inspired/expired oxygen signal can be applied using knowledge of the tracheal dead-space gas. For present purposes, the expired gas is assumed to be substantially at body temperature and at 100% relative humidity. The first gas that is expired at the mouth during every breath is gas that had remained in the trachea and did not participate in gas exchange. This "tracheal gas" is essentially inspired gas that has been heated to body temperature and completely humidified by the trachea, but has not had any oxygen removed by the lungs. The difference between the oxygen fraction of inspired gas and the oxygen fraction of the tracheal gas corresponds to the amount of compensation that must be applied to correct the inspired gas to the expired gas temperature and humidity conditions.

As an example, the inspiratory portion of the oxygram may be corrected to expiratory conditions by:

1. Measurement of the difference between the oxygen concentration of inspired gas and the oxygen concentration of tracheal gas.

2. Subtraction the difference measured in step 1 from the next, or currently displayed, oxygen waveform values. Also subtract the measured difference from the inspired oxygen parameter ($FiO_2$). It is further contemplated that instead of subtracting the difference, the ratio of wet (tracheal) to dry (inspired) oxygen concentration could be used as multiplier of the uncorrected waveform.

3. Display the oxygen waveform with the measured expired and compensated inspired data. It is contemplated that the flow signal can be used to determine the exact transition time between inspired and expired gas flow.

Figure 9:
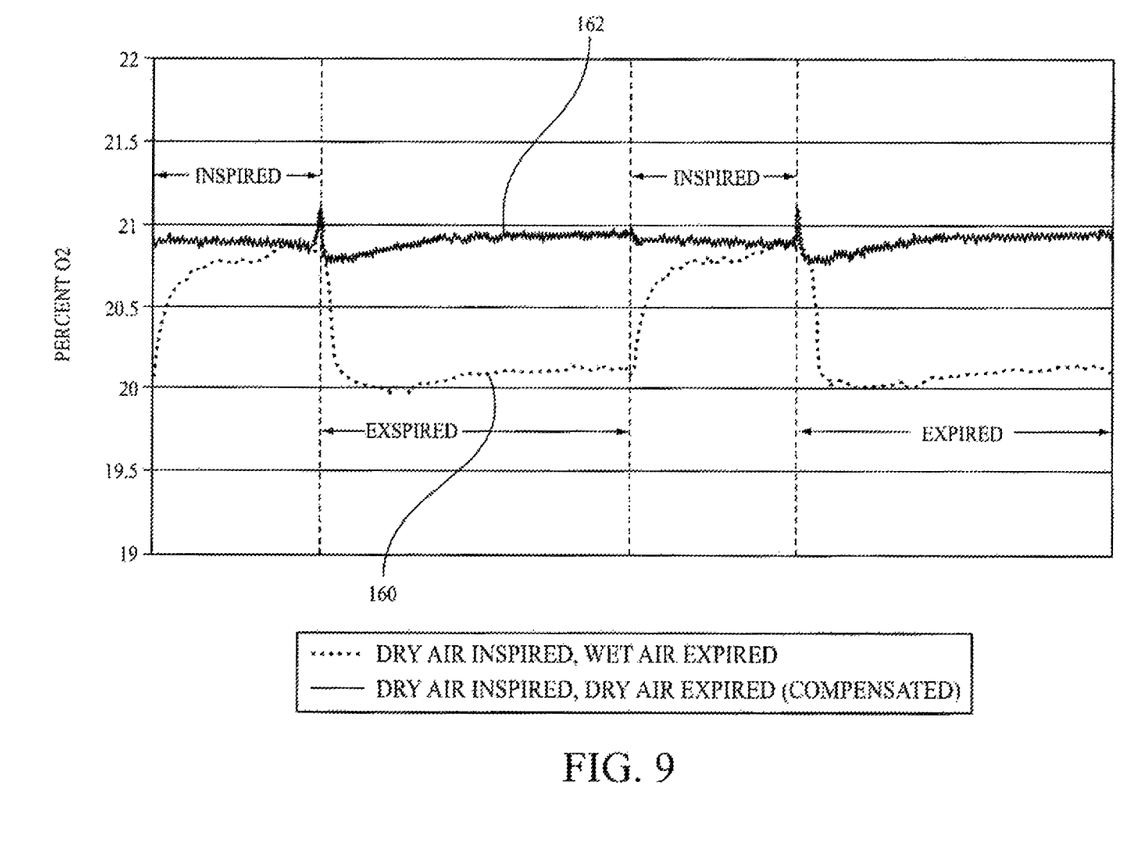
FIG. 9 is a graph showing two exemplary oxygen percent waveforms created by mechanically ventilating a test lung with dry room air and adding humidification to the gas exiting the test lung.

FIG. 9 is a graph illustrating two exemplary oxygrams (oxygen percent waveforms), corrected and non-corrected, created by mechanically ventilating a test lung with dry room air and adding humidification to the gas exiting the test lung. Oxygram 160 represents a waveform in which the inspiration of dry air and expiration of wet air is not corrected for the differences between inspiratory and expiratory gas due to humidification. If oxygram 160 is corrected for the differences according to the principles of the present invention, oxygram 162 results. It can be observed in this exemplary figure that the applied correction reduces the apparent fluctuation of percent oxygen from approximately 1% to approximately 0.1%.

The present invention also contemplates that both the compensated inspired and measured expired oxygen parameters (and oxygram waveform) can be adjusted to ambient conditions. Because the expired gas is at a substantially known temperature and humidity, it can be adjusted numerically to ambient conditions prior to display. After applying the compensation described above to the inspired data, the same numerical adjustment as was applied to the expired waveform and parameters can be applied to the inspired oxygen data. The resulting waveform and parameters mirrors the conditions of the side-sampled waveform to which clinicians are accustomed to visualizing.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of monitoring an analyte in a gas flow comprising the acts of:
providing mainstream airway adapter having the gas flow therethrough;
producing by a gas sensing portion a signal indicative of the analyte in the gas flow;
determining by a processing portion an amount of the analyte in the gas flow based on the signal from the gas sensing portion;
compensating by the processing portion for volumetric differences between the gas flow during inspiration and the gas flow during expiration; and
outputting a signal indicative of the amount of analyte in a human perceivable format,
wherein the compensating act includes monitoring a tracheal dead space gas and using the monitored tracheal dead space gas to determine a difference between an analyte fraction of inspired gas and an analyte fraction of the tracheal dead space gas for determining the amount of the analyte in the gas flow.

2. The method of claim 1, wherein the first portion of gas exhaled during the expiration is a remaining gas of inspired gas, where the remaining gas has remained in a trachea and has been heated to body temperature and humidified by the trachea, and did not participate in gas exchange in lungs where oxygen has not been removed by lungs from the remaining gas.

3. The method of claim 1, wherein the analyte is oxygen, and the method further comprising the act of determining oxygen consumption ($VO_2$) based on the amount of analyte.

4. The method of claim 1, further comprising the act of determining a flow rate of the gas flow, and wherein determining the amount of the analyte includes the acts of:
determining oxygen concentration in the gas flow; and
determining carbon dioxide in the gas flow.

5. The method of claim 4, further comprising the act of determining oxygen consumption $VO_2$ as:

$$VO_2 = V_E * Fi_{O2\_DS} - *((1-Fe_{CO2}-Fe_{O2})/(1-Fi_{CO2}-Fi_{O2\_DS}))-Fe_{O2}],$$

where $V_E$ is an expired volume of gas, $Fi_{O2\_DS}$ is a tracheal dead space oxygen concentration, $Fe_{CO2}$ is an expired carbon dioxide concentration, $Fe_{O2}$ is an expired oxygen concentration, and $Fi_{CO2}$ is an inspired carbon dioxide concentration.

6. The method of claim 1, wherein the act of determining the amount of the analyte in the gas flow based on the signal from the gas sensing portion includes the acts of:
exciting a luminescable material with an excitation energy; and
monitoring quenching of a luminescence.

7. The method of claim 1, further comprising the act of determining a flow rate of the gas flow, and wherein the act of determining the amount of the analyte includes determining an oxygen concentration in the gas flow.

8. The method of claim 7, further comprising the act of determining oxygen consumption $VO_2$ as;

$$VO_2 = V_i * Fi_{O2\_DS} - Ve * Fe_{O2},$$

where Vi is an inspired volume of gas, $Fi_{O2\_DS}$ is a tracheal dead space oxygen concentration, $V_E$ is an expired volume of gas, and $Fe_{O2}$ is an expired oxygen concentration.

* * * * *